(12) United States Patent
Brechbiel et al.

(10) Patent No.: US 8,454,936 B2
(45) Date of Patent: Jun. 4, 2013

(54) METAL CHELATORS AND METHODS OF THEIR USE

(75) Inventors: Martin Wade Brechbiel, Annandale, VA (US); Thomas Clifford, Rockville, MD (US)

(73) Assignee: The United States of America, as represented by the Secretary, Department of Health And Human Services, Washington, DC (US)

( * ) Notice: Subject to any disclaimer, the term of this patent is extended or adjusted under 35 U.S.C. 154(b) by 178 days.

(21) Appl. No.: 12/752,419

(22) Filed: Apr. 1, 2010

(65) Prior Publication Data

US 2010/0189645 A1    Jul. 29, 2010

Related U.S. Application Data

(62) Division of application No. 11/659,601, filed as application No. PCT/US2005/028125 on Aug. 9, 2005, now Pat. No. 7,785,565.

(60) Provisional application No. 60/600,253, filed on Aug. 10, 2004, provisional application No. 60/603,781, filed on Aug. 23, 2004.

(51) Int. Cl.
*A61B 5/055* (2006.01)

(52) U.S. Cl.
USPC ......... 424/9.3; 424/1.11; 424/1.65; 424/1.69; 424/1.73; 424/9.1; 424/9.4

(58) Field of Classification Search
USPC .................... 424/1.11, 1.49, 1.65, 1.69, 1.73, 424/9.1, 9.2, 9.3, 9.4, 9.5, 9.6, 9.7, 9.8; 530/300–350; 534/7, 10–16; 514/1, 1.1
See application file for complete search history.

(56) References Cited

U.S. PATENT DOCUMENTS

| | | | |
|---|---|---|---|
| 5,246,692 A | 9/1993 | Gansow et al. | |
| 5,556,939 A | 9/1996 | Flanagan et al. | |
| 6,696,551 B1 | 2/2004 | Brechbiel et al. | |
| 6,765,104 B1 | 7/2004 | Brechbiel et al. | |
| 6,852,842 B2 | 2/2005 | Brechbiel et al. | |
| 6,995,247 B2 | 2/2006 | Brechbiel et al. | |
| 7,368,100 B2 | 5/2008 | Brechbiel et al. | |
| 7,785,565 B2 * | 8/2010 | Brechbiel et al. | 424/1.65 |

FOREIGN PATENT DOCUMENTS

WO    WO 01/10870 A1    2/2001
WO    WO 2004/022106 A1    3/2004

OTHER PUBLICATIONS

Brechbiel, M.W. et al., "Chelating agent for labelling of monoclonal antibody with 212 Bi for -particle mediated radioimmunotherapy," J. Chem Soc. Chem. Commun., 1991, 1169-1170.
Brechbiel, M.W., et al., "An effective chelating agent for labelling of monoclonal antibody with $^{212}$Bi for a-particle mediated radioimmunotherapy," J. Chem. Soc. Chem. Commun., 1991, 1169-1170.
Brechbiel, M.W., et al., Metal chelators and target-moiety complexes for imaging, Feb. 2007, 2 pages.
Chong, H.S., et al., "Synthesis and evaluation of novel macrocyclic and acyclic ligands as contrast enhancement agents for magnetic resonance imaging", 2006, 49(6), 2055-62.
Clifford, T., et al., "A chelate suitable for preparation of metal ion labeled peptides in conventional peptide synthesizers", Radiation Oncology Branch, National Cancer Institute, Presented in Philadelphia on Aug. 24, 2004. Poster.
Clifford, T., et al., "Validation of a novel CHX-A" derivative suitable for peptide conjugation: small animal PET/CT imaging using yttrium-86-CHX-A-octreotide., J. Med. Chem., 2006, 49(14), 4297-304.

(Continued)

*Primary Examiner* — D L Jones
(74) *Attorney, Agent, or Firm* — Woodcock Washburn LLP

(57) ABSTRACT

Metal chelators of Formula I and Formula II are disclosed:

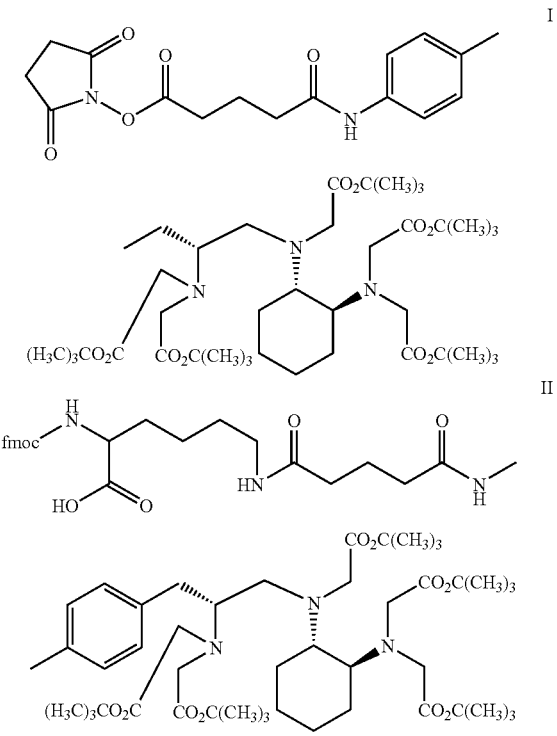

or a pharmaceutically acceptable salt thereof.

Also disclosed are metal chelator-targeting moiety complexes, metal chelator-targeting moiety-metal conjugates, kits, and methods of their preparation and use in diagnosis and/or treatment of diseases and conditions, including, inter alia, cancer and thrombosis.

24 Claims, No Drawings

OTHER PUBLICATIONS

De León-Rodriguez L.M., et al., "Solid-phase synthesis of DOTA-peptides," Chemistry, Weinheim An Der Bergstrasse, Germany, 2004, 10(5), 1149-1155.

Frechet, J.M.J. (Ed.), *Dendrimers and Other Dendritic Polymers*, NY, John Wiley & Sons, 2002, Tomalia, D.A. (Ed.), http://www.dendritch.com/pamam.html, down loaded from the internet on Aug. 16, 2004, 2 pages.

Gennaro, A.R., *Remington's Pharmaceutical Sciences*, 17$^{th}$ Ed., Mack Publishing Company, Easton, PA, 1985, Chp. 85, 1518-1677.

Golub et al., Science, Oct. 15, 1999, pp. 531-537.

Greene, T.W., et al., *Protective Groups in Organic Synthesis*, 2$^{nd}$ Ed, Wiley & Sons, 1991, 10-142.

Milenic, D.E., et al., "In vivo comparison of macrocyclic and acyclic ligands for radiolabeling of monoclonal antibodies with $^{177}$Lu for radioimmunotherapeutic applications," Nucl. Med. Biol., 2002, 29, 431-442.

Pathare, P.M., et al., "Synthesis and radiolabeling of a Biotin-Chx-B chelate for BI-213," J. of Labelled Compounds & Radiopharmaceuticals, Sussex, GB, 1998, 41(7), 595-603.

Radioisotopes in Medicine, 2004, http://www.uic.com.au/nip26.htm, downloaded from the internet on Aug. 16, 2004, 9 pages.

Rana, T.M., et al., "Synthesis of a metal-ligating amino acid suitable for solid phase assembly of peptides," Tetrahedron Letters, 1992, 33(32), 4521-4524.

Wu, C., et al., "Stereochemical influence on the stability of radio-metal complexes in vivo. Synthesis and evaluation of the four stereoisomers of 2-(p-nitrobenzyl)-trans-CyDTPA," Bioorg. Med. Chem., 1997, 5(10), 1925-1934.

Young, K.K., et al., "New hybrid ligands with a trans-1,2-diaminocyclohexane backbone: competing chelation modes in palladium-catalyzed enantioselective allylic alkylation," J. Org Chem., 2000, 65, 7807-7813.

\* cited by examiner

US 8,454,936 B2

METAL CHELATORS AND METHODS OF THEIR USE

CROSS REFERENCE TO RELATED APPLICATIONS

The application is a divisional of U.S. application Ser. No. 11/659,601 filed Feb. 6, 2008 which claims priority to U.S. Application No. 60/600,253 filed Aug. 10, 2004 and to U.S. Application No. 60/603,781 filed Aug. 23, 2004, the entire disclosures of which are incorporated herein by reference.

STATEMENT OF FEDERALLY SPONSORED RESEARCH

The U.S. Government may have certain rights in the invention described herein, which was made in part with funds from NIH Contract No. 263-02-D-0053.

FIELD OF THE INVENTION

The present invention relates to metal chelators, metal chelators-targeting moiety complexes, metal chelators-targeting moiety-metal conjugates, kits, and methods of their preparation and use in diagnosis and/or treatment of diseases and conditions, including, inter alia, cancer and thrombosis.

BACKGROUND OF THE INVENTION

Direct imaging of many biochemical processes is now practicable through the use of radiopharmaceuticals targeted towards specific disease-associated molecular targets. This was made possible by the discoveries in the field of disease related changes in cellular communication and metabolism, especially in cancer. To support these new diagnostic applications, methods for linking radioisotopes to the appropriate targeting biomolecules were required to replace the simple metal chelates and ions used previously. In the 1980s and 1990s, methods were developed for labeling biomolecules, especially monoclonal antibodies, with radionuclides such as technetium-99m ($^{99m}$Tc) and indium-111 ($^{111}$In). In its most developed form, this typically entailed covalent attachment of a bifunctional chelator to a protein, followed by labeling with the radiometal, or even synthesis of a radiometal bifunctional chelate that was subsequently attached to the protein. As recognition grew in the 1980s that monoclonal antibodies were too large to offer ideal pharmacokinetics, focus shifted onto smaller molecules, such as antibody fragments and especially smaller peptides, targeted towards receptors present in lesions such as tumors and thrombi. Examples include radiolabeled octatreotide (selective for somatostatin receptors expressed by tumors of the endocrine system such as paragangliomas and neuroblastomas), bombesin (receptors for this peptide are expressed by small-cell lung carcinomas), and α-melanocyte stimulating hormone (expressed by melanomas).

Although the transition to smaller molecules brought with it the opportunity to use peptides produced by solid phase peptide synthesis (SPPS) rather than proteins of biological origin, the same methods were used to label them as had been used to label antibodies. These methods have several disadvantages, which are more problematic with small peptides than with large proteins. The most suitable sites for attachment of a bifunctional chelator in most peptides are the ε-amino groups of lysine residues and the N-terminus, because they are very reactive nucleophiles and form very unreactive covalent links with the chelator. If there is more than one lysine in the peptide chain, the site of modification becomes uncertain. For instance, if the peptide has two lysines, together with the N-terminus these will present three possible sites for conjugation, hence forming as many as eight products when treated with an active-ester-containing bifunctional chelator or radiolabeled bifunctional chelate. Each of these products will have a different biodistribution and different affinities for the target (some of which may have lost all target affinity) and such a mixture is not acceptable for clinical use. Moreover, one or more of the lysines may be essential to the biological activity of the peptide. A simple solution has been to incorporate the chelator, or a radiolabeled chelate or organic prosthetic group, as the last step of SPPS. This, however, has the limitation that the chelator has to be at one end of the peptide chain, which is frequently essential to the biological activity of the peptide.

The state of the art in linking radiometals to peptides encompasses a number of approaches. Some have the advantage of incorporating the metal binding sequence during SPPS, and others have the advantage of incorporating chelators that are specifically designed for the particular metal. Few, however, have both of these advantages. For example, technetium-chelating amino acid sequences such as gly-gly-cys are incorporated during SPPS or recombinant protein production, but this sequence is not ideal for its purpose, and merely represents the best that can be achieved for chelating the TcO$^{3+}$ core using "standard" amino acids (i.e. those coded through tRNAs). Likewise, polyhistidine sequences, such as hexahistidine, can be incorporated during SPPS, but again they merely represent the best sequence of coded amino acids achievable for chelating the Tc(CO)$_3^+$ core. Conversely, the synthetic technetium ligand hynic (hydrazinonicotinamide) probably represents the most convenient and efficient labeling system to date for use with $^{99m}$Tc, but it has so far only been used by conjugating it to a pre-formed peptide, with all the associated problems outlined above. An alternative that offers convenience of labeling is the "direct labeling" method in which antibodies and peptides containing disulfide bonds can be reduced and labeled with $^{99m}$Tc or $^{188}$Re. However, the chemistry of these methods is poorly understood, and there are major stability and biological activity problems as demonstrated by the work of several groups world wide with antibodies and somatostatin analogues.

WO 2004/022106 discloses technology that incorporates the metal binding moiety during SPPS and incorporates chelators that are specifically designed for the particular metal. More specifically, WO 2004/022106 discloses metal-chelating precursors, designed to bind specific metallic radionuclides and incorporating a pendant protected (e.g. Fmoc) amino acid functionality. The chelator is attached to an amino acid before rather than after SPPS assembly of the peptide chain. A chelator-derivatized amino acid comprises: 1) an optionally protected primary or secondary amino group; 2) a carboxylic acid group; 3) a chelator group capable of binding a metallic radionuclide. Suitable chelating or metal binding groups may be chosen from several structures including but not limited to the hydrazinonicotinamide group, di- or polythiol groups, macrocyclic ligands incorporating amine, thioether, or phosphine donor groups, or polyaminocarboxylate groups.

As discussed above, there is a continuing need for more versatile and controlled approaches to the synthesis of metal conjugates useful, inter alia, in the diagnosis and/or treatment of diseases and conditions. The present invention focuses on novel compounds directed to these and other important uses.

SUMMARY OF THE INVENTION

The present invention is directed to metal chelators, metal chelator-targeting moiety complexes, metal chelator-targeting moiety-metal conjugates, kits, and methods of their preparation and use in diagnosis and/or treatment of diseases and conditions, including, inter alia, cancer and thrombosis. The metal chelators may be used in conventional synthetic methods, inter alia, to form targeting moieties, such as peptides, proteins, and amine-surface functional dendrimers, capable of conjugating diagnostic and/or therapeutic metals.

In one embodiment, the invention is directed to compounds of Formula I and II:

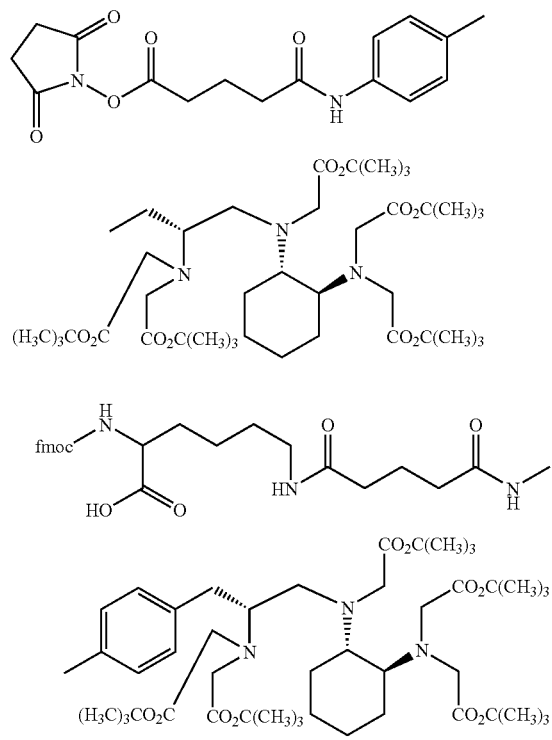

or a pharmaceutically acceptable salt thereof.

In another embodiment, the invention is directed to complexes, comprising:
a. at least one targeting moiety selected from the group consisting of peptide, protein, and an amine-surface functional dendrimer; and
b. a residue of a compound of Formula I or Formula II or a pharmaceutically acceptable salt thereof;
wherein said compound is covalently linked to said targeting moiety.

In other embodiments, the invention is directed to conjugates, comprising:
a. at least one targeting moiety selected from the group consisting of peptide, protein, and amine-surface functional dendrimer;
b. a residue of a compound of Formula I or Formula II or a pharmaceutically acceptable salt thereof;
wherein said compound is covalently linked to said targeting moiety; and
c. a diagnostic or therapeutic metal.

In other embodiments, the invention is directed to compositions, comprising:
a. a complex comprising:
  i. at least one targeting moiety selected from the group consisting of peptide, protein, and amine-surface functional dendrimer; and
  ii. a residue of a compound of Formula I or Formula II or a pharmaceutically acceptable salt thereof;
  wherein said compound is covalently linked to said targeting moiety; and
b. a pharmaceutically-acceptable carrier.

In another embodiment, the invention is directed to compositions, comprising:
a. a conjugate, comprising:
  i. at least one targeting moiety selected from the group consisting of peptide, protein, and amine-surface functional dendrimer;
  ii. a residue of a compound of Formula I or Formula II or a pharmaceutically acceptable salt thereof;
  wherein said compound is covalently linked to said targeting moiety; and
  iii. a diagnostic or therapeutic metal; and
b. a pharmaceutically-acceptable carrier.

In yet other embodiments, the invention is directed to kits for detecting, imaging, monitoring, or treating a disease or condition in a patient comprising:
a. a complex comprising:
  i. at least one targeting moiety selected from the group consisting of peptide, protein, and amine-surface functional dendrimer; and
  ii. a residue of a compound of Formula I or Formula II or a pharmaceutically acceptable salt thereof;
  wherein said compound is covalently linked to said targeting moiety;
b. a therapeutic or diagnostic metal;
c. an optional pharmaceutically-acceptable carrier; and
d. instructions for preparing a composition comprising a therapeutic or diagnostic agent for detecting, imaging, monitoring, or treating a disease or condition in a patient.

In yet other embodiments, the invention is directed to kits for detecting, imaging, monitoring, or treating a disease or condition in a patient comprising:
a. a conjugate comprising:
  i. at least one targeting moiety selected from the group consisting of peptide, protein, and amine-surface functional dendrimer; and
  ii. a residue of a compound of Formula I or Formula II or a pharmaceutically acceptable salt thereof;
  iii. a diagnostic or therapeutic metal;
  wherein said compound is covalently linked to said targeting moiety;
b. an optional pharmaceutically-acceptable carrier; and
c. instructions for preparing a composition comprising a therapeutic or diagnostic agent for detecting, imaging, monitoring, or treating a disease or condition in a patient.

In other embodiments, the invention is directed to processes of synthesizing peptides or proteins comprising a chelator, said processes comprising the step of:
incorporating into said peptides or proteins a residue of a compound of Formula I or Formula II or a pharmaceutically acceptable salt thereof.

In other embodiments, the invention is directed to processes of synthesizing amine-surface functional dendrimers comprising a chelator, said processes comprising the step of:
incorporating into said amine-surface functional dendrimer a residue of a compound of Formula I or Formula II or a pharmaceutically acceptable salt thereof.

In yet another embodiment, the invention is directed to conjugates of the peptides, proteins, and amine-surface functional dendrimers produced by the above-described processes.

In other embodiments, the invention is directed to methods of detecting, imaging or monitoring cancer in a patient, comprising the steps of:
a. administering to said patient a conjugate described above; and
b. acquiring an image of a site of concentration of said conjugate in the patient by a diagnostic imaging technique.

In other embodiments, the invention is directed to methods of detecting, imaging or monitoring thrombi in a patient, comprising the steps of:
a. administering to said patient a conjugate described above; and
b. acquiring an image of a site of concentration of said conjugate in the patient by a diagnostic imaging technique.

In yet other embodiments, the invention is directed to methods of treating cancer, comprising the step of:
administering to a patient in need thereof an effective amount of a conjugate described above.

DETAILED DESCRIPTION OF THE INVENTION

The present invention is directed to metal chelators, metal chelator-targeting moiety complexes, metal chelator-targeting moiety-metal conjugates, and methods of their preparation and use in diagnosis and/or treatment of diseases and conditions, including, inter alia, cancer and thrombosis. The metal chelators may be used in conventional synthetic methods, inter alia, to form targeting moieties, such as peptides, proteins, and amine-surface functional dendrimers, capable of conjugating diagnostic and/or therapeutic metals. The following definitions are provided for the full understanding of terms and abbreviations used in this specification.

Definitions

As used herein and in the appended claims, the singular forms "a," "an," and "the" include the plural reference unless the context clearly indicates otherwise. Thus, for example, a reference to "a compound" is a reference to one or more compounds and equivalents thereof known to those skilled in the art, and so forth.

As used herein, the term "therapeutic agent" refers to an agent that may be used to prevent cure, alleviate the onset and/or progression of a condition(s), pathological disorder(s) or disease(s).

As used herein, the term "diagnostic agent" refers to an agent that may be used to detect, image and/or monitor the presence and/or progression of a condition(s), pathological disorder(s) or disease(s).

A "chelator" is the moiety or group on a reagent that binds to a metal ion through the formation of chemical bonds with one or more donor atoms.

As used herein, the phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable salts" refers to salts prepared from pharmaceutically acceptable non-toxic acids, including inorganic salts, and organic salts. Suitable non-organic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and the like. Particularly preferred are hydrochloric, hydrobromic, phosphoric, and sulfuric acids, and most preferably is the hydrochloride salt.

As used herein, term "administering" means either directly administering a compound, complex, conjugate, or composition of the present invention, or administering a prodrug, derivative or analog that will form an equivalent amount of the active compound or substance within the body.

The term "effective amount," as used herein, refers to an amount effective, at dosages, and for periods of time necessary, to achieve the desired result with respect to the therapeutic or diagnostic treatment.

As used herein, the term "subject" or "patient" refers to an animal including the human species that is treatable with the compositions, and/or methods of the present invention. The term "subject" or "subjects" is intended to refer to both the male and female gender unless one gender is specifically indicated. Accordingly, the term "patient" comprises any mammal that may benefit from diagnosis and/or therapy using the metal chelators of the invention.

Metal Chelator Compounds

In one embodiment, the invention is directed to compounds of Formula I and II:

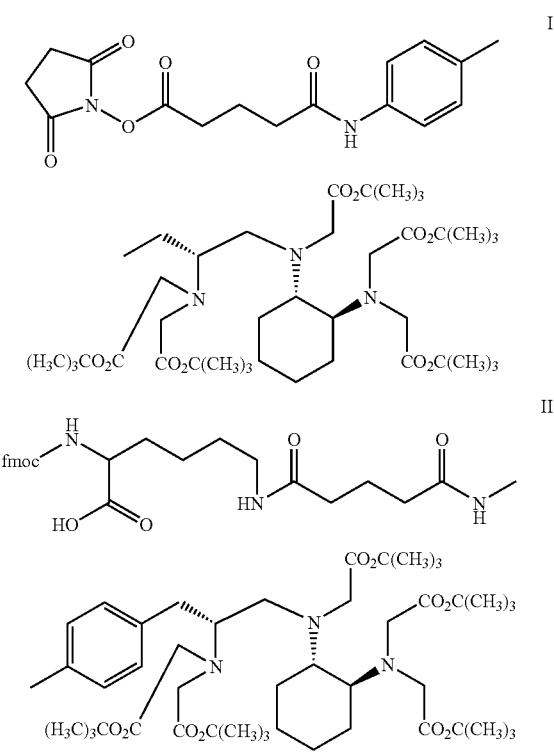

or a pharmaceutically acceptable salt thereof.

The invention also contemplates the deprotected compound of Formula II, where the fmoc group is not present and is replaced by a hydrogen atom. Thus, the "compound of Formula II," as used herein, includes the deprotected analog of the compound of Formula II:

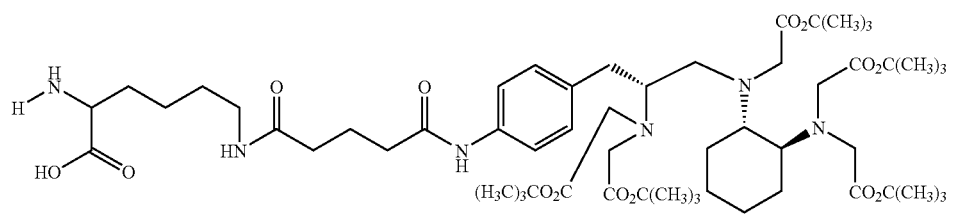
The metal chelator compound of Formula I may be prepared in accordance with the general synthetic scheme shown in Scheme 1.
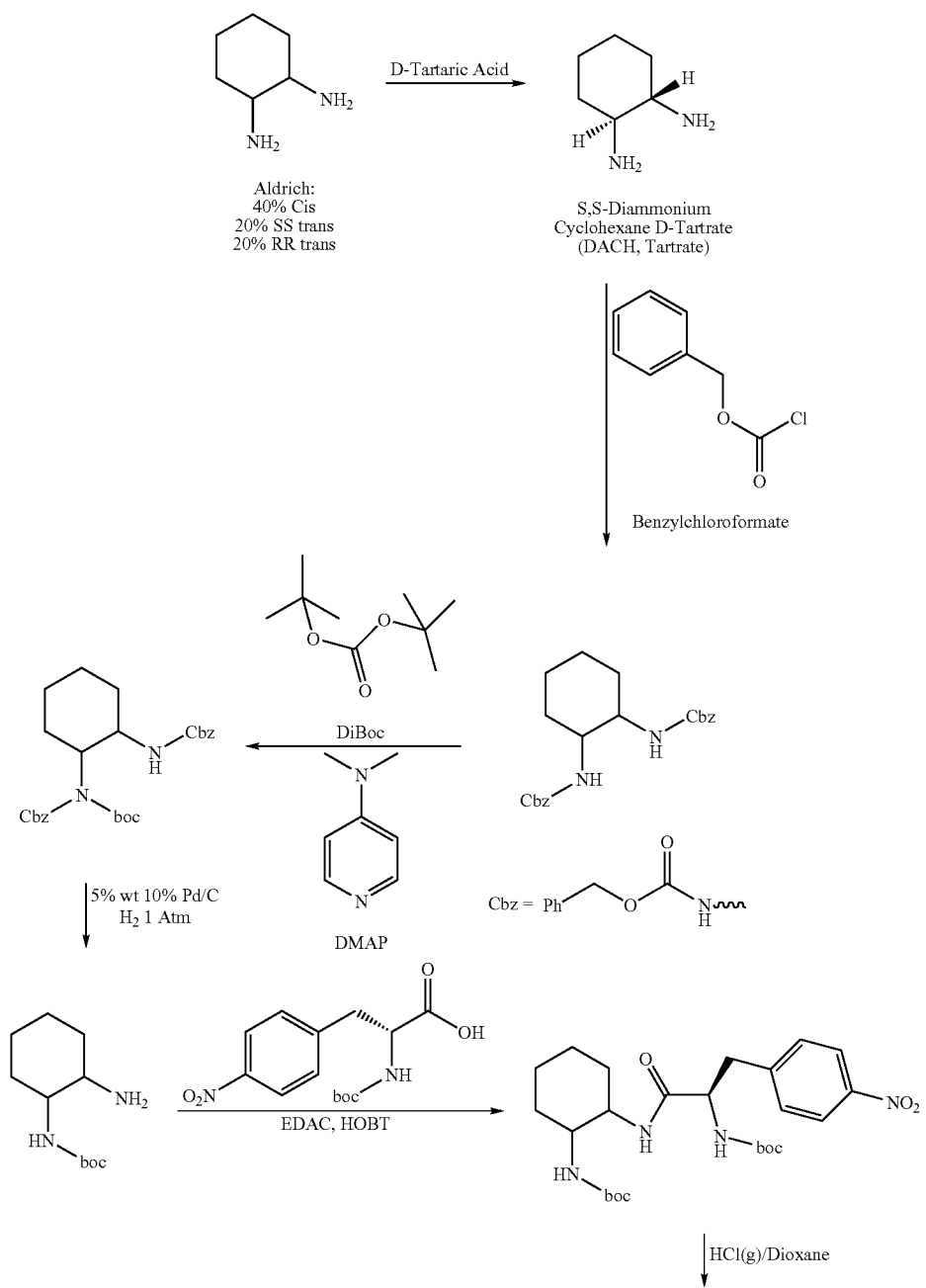

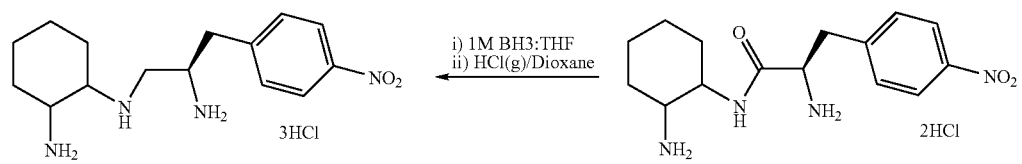
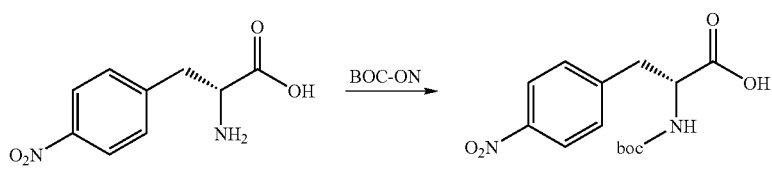
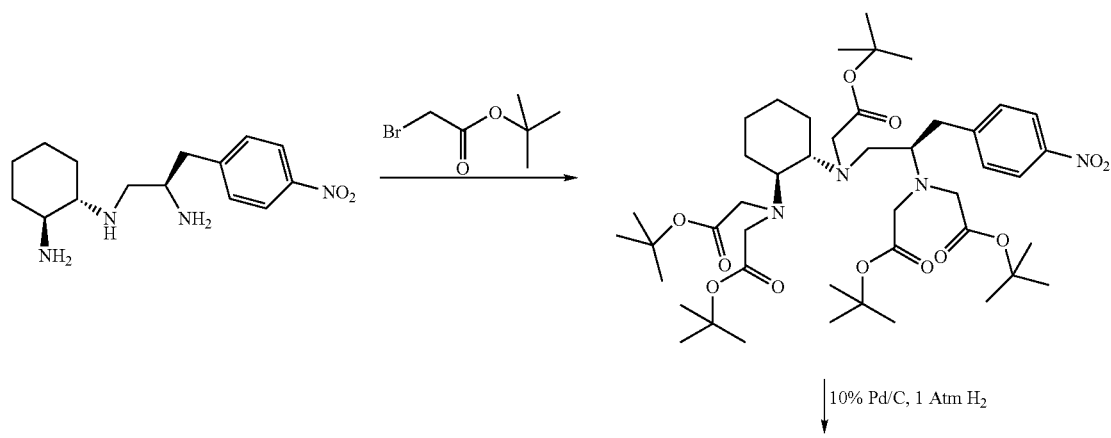
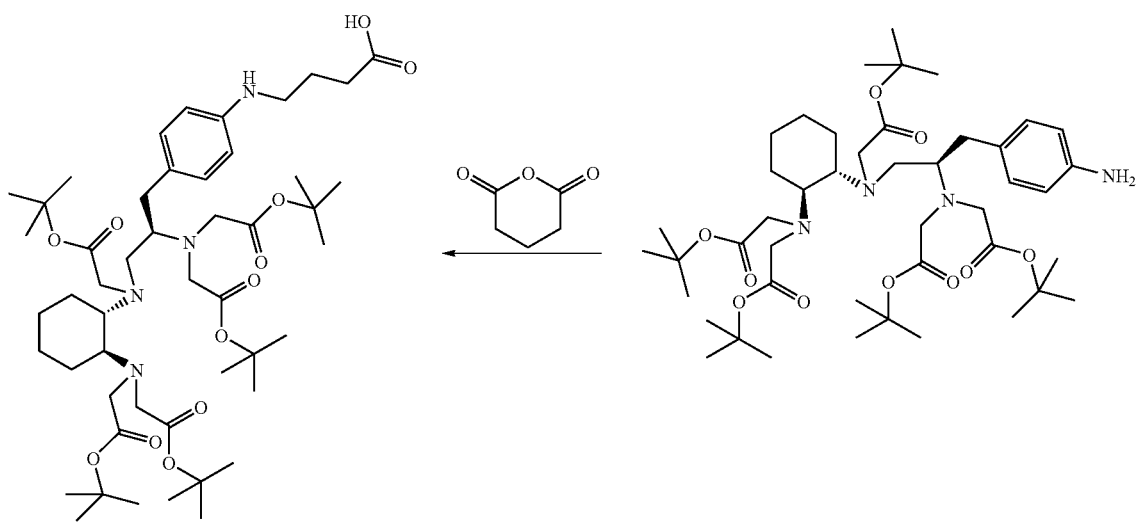
key intermediate
[3]
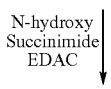
N-hydroxy Succinimide
EDAC -continued

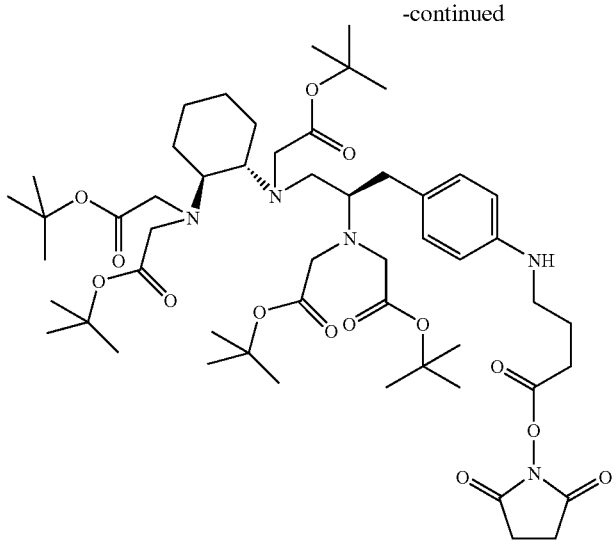

The synthesis of the compound of Formula I is completed by fully alkylating the amines with bromoacetate t-butyl ester, hydrogenation of the nitro group, and reaction of the aniline with glutaric anhydride, simultaneously protecting the aniline nitrogen as an amide and providing a terminal carboxylate suitable for conversion to an activated ester. COESY NMR spectra of the carboxylic acid intermediate shows a triplet-pentet-triplet pattern of the glutaryl-linking moiety.

In certain preferred embodiments, a specific enantiomer (S,S-cyclohexyl-R-p-nitrophenylalenyl) is prepared. Aminocarboxylate chelates with this specific enantiomeric backbone are preferred because of their superior metal ion complexation stability.

1. Wu, C., Kobayashi, H., Sun, B., Yoo, T. M., Paik, C. H., Gansow, O. A., Carrasquillo, J. A., Pastan, I., Brechbiel, M. W.: Stereochemical Influence on the Stability of Radio-Metal Complexes In Vivo. Synthesis and Evaluation of the Four Stereoisomers of 2-(p-nitrobenzyl)-trans-CyDTPA. *Bioorg. Med. Chem.* 1997, 5, 1925-1934.
2. Brechbiel, M. W., Pippin, C. G., McMurry, T. J., Milenic, D., Roselli, M., Colcher, D., Gansow, O. A.: An Effective Chelating Agent for Labeling of Monoclonal Antibody with [212]Bi for a-Particle Mediated Radioimmunotherapy. *J. Chem. Soc., Chem. Commun.* 1991, 1169-1170.
3. Milenic, D. E., Garmestani, K., Chappell, L. L., Dadachova, E., Yordanov. A., Ma, D., Schlom, J., Brechbiel, M. W. In Vivo Comparison of Macrocyclic and Acyclic Ligands for Radiolabeling of Monoclonal Antibodies with $^{177}$Lu for Radioimmunotherapeutic Applications. *Nucl. Med. Biol.* 2002, 29, 431-442.

The metal chelator compound of Formula II may be prepared by mixing a compound of Formula I with a commercially-available sample of an 9-fluorenylmethoxycarbonyl (FMOC or fmoc) protected lysine to yield a compound of Formula II. The compound of Formula II may be deprotected by any conventional techniques for removing FMOC protecting groups, including, for example, treatment with base such as 20-50% piperidine in dimethylformamide (DMF) for about 20 minutes. In the case of incomplete fmoc deprotection, a stronger base, such as 1,8-diazabicyclo[5.4.0]undec-7-ene (DBU) with 2% piperidine, may be used.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

It should be understood that the compounds of this invention may be modified by appending appropriate chemical groups to enhance selective biological properties. Such modifications are known in the art and include those that increase biological penetration into a given biological compartment (e.g., blood, lymphatic system, central nervous system), increase oral availability, increase solubility to allow administration by injection, alter metabolism and alter rate of excretion.

It should also be understood that the compounds of this invention may adopt a variety of conformational and ionic forms in solution, in pharmaceutical compositions and in vivo. Although the depictions herein of specific compounds of this invention are of particular conformations and ionic forms, other conformations and ionic forms of those compounds are envisioned and embraced by those depictions.

Metal Chelator-Targeting Moiety Complexes

In another embodiment, the invention is directed to complexes, comprising:
a. at least one targeting moiety selected from the group consisting of peptide, protein, and amine-surface functional dendrimer; and
b. a residue of a compound of Formula I or Formula II or a pharmaceutically acceptable salt thereof;

wherein said compound is covalently linked to said targeting moiety.

The compound of Formula I may be incorporated at the end of the chain(s) of the peptide, protein, or amine-surface functional dendrimer. Compound of Formula II may be incorporated either at the end or within the chain(s) of the peptide, protein, or amine-surface functional dendrimer.

In certain embodiments, the targeting moiety is poly(amidoamine) dendrimer (PAMAM), octatreotide, bombesin, or α-melanocyte stimulating hormone and the residue of a compound of Formula I or Formula II is incorporated at the end of the peptide/dendrimer or the compound of Formula II is incorporated within the peptide/dendrimer backbone.

In certain embodiment of the complex, the residue of a compound of Formula I or Formula II is linked to the targeting moiety via a terminal amino group on the targeting moiety, preferably via an N-terminus of the targeting moiety, a lysine residue on the targeting moiety, or shell amine of an amine-surface functional dendrimer.

In certain other embodiment of the complex, the residue of a compound of Formula II may be linked to the targeting moiety at any pre-determined point in the sequence of the targeting moiety, including at the N-terminal, between two units of amino acids, or on a lysine residue. When a compound of Formula II is used, a single complex may contain more than one unit of a compound of Formula II, for example at the N-terminal and between two units of amino acids.

In other embodiments, the invention is directed to processes of synthesizing peptides or proteins comprising a chelator, said processes comprising the step of:
incorporating into said peptides or proteins a residue of a compound of Formula I or Formula II.

In other embodiments, the invention is directed to processes of synthesizing amine-surface functional dendrimers comprising a chelator, said processes comprising the step of:
incorporating into said amine-surface functional dendrimer a residue of a compound of Formula I or Formula II or a pharmaceutically acceptable salt thereof.

In yet another embodiment, the invention is directed to complexes of peptides, proteins, and amine-surface functional dendrimers produced by the above-described processes.

Typically, the complex will be synthesized prior to chelation of the therapeutic or diagnostic metal. However, the present invention contemplates the chelation of the therapeutic or diagnostic metal to the compound of Formula I or Formula II or a pharmaceutically acceptable salt thereof prior to synthesis of the complex.

Preferably, when the targeting moiety is a peptide or protein, it may be synthesized by solid phase peptide synthesis (SPPS), such as described in Atherton, E., Sheppard, R. C., *Solid phase peptide synthesis: a practical approach*. IRL Press at Oxford University Press (1989). An example is shown below with a compound of Formula I:

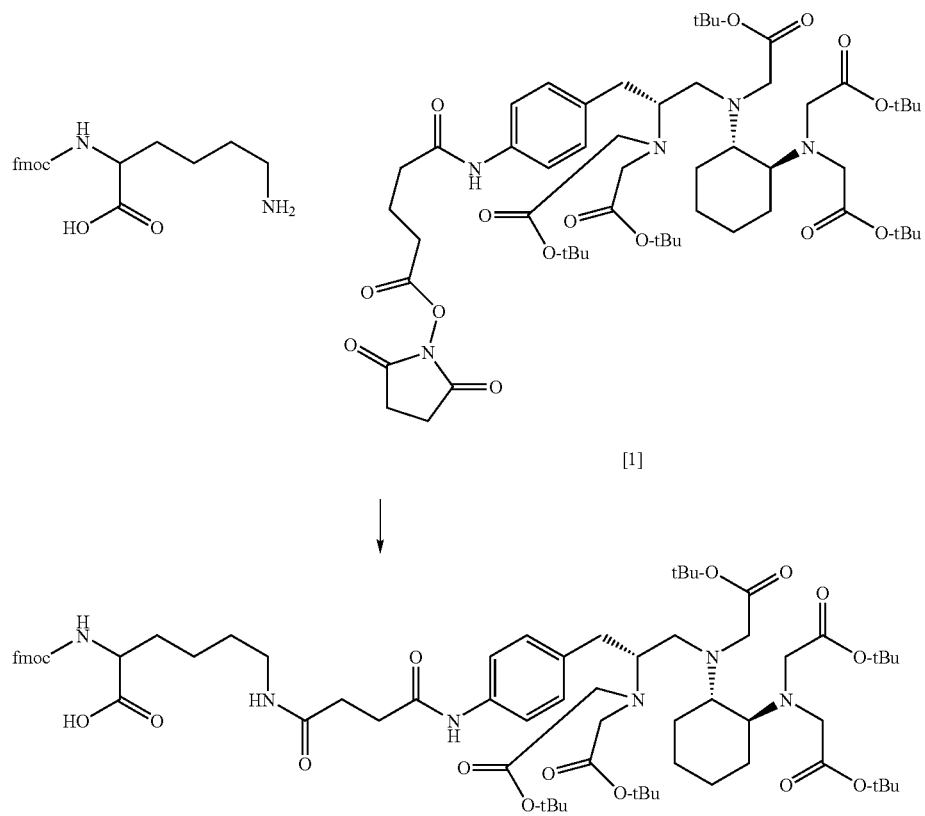

The amine-surface functional dendrimers, preferably PAMAM-type, may be prepared by conventional synthetic techniques, such as those described in Jean M. J. Frechet (editor), Donald A. Tomalia (editor), *Dendrimers and Other Dendritic Polymers* (New York: John Wiley & Sons, 2002).

The method of the present invention is advantageous over conventional post-SPPS conjugation in at least the following ways:
1. The method is versatile and flexible: it incorporates the chelator site-specifically anywhere in sequence in the case of the chelator compound of Formula II, not just terminally or at one or more lysines.
2. It can leave lysines unmodified.
3. It is economic since no post-SPPS modification is needed.

Metal Chelator-Targeting Moiety-Metal Conjugates

In other embodiments, the invention is directed to conjugates, comprising:
a. at least one targeting moiety selected from the group consisting of peptide, protein, and amine-surface functional dendrimer;

b. a residue of a compound of Formula I or Formula II or a pharmaceutically acceptable salt thereof;
   wherein said compound is covalently linked to said targeting moiety; and
c. a diagnostic or therapeutic metal.

In other embodiments, the invention is directed to compositions, comprising:
a. a complex comprising:
   i. at least one targeting moiety selected from the group consisting of peptide, protein, and amine-surface functional dendrimer; and
   ii. a residue of a compound of Formula I or Formula II or a pharmaceutically acceptable salt thereof;
      wherein said compound is covalently linked to said targeting moiety; and
b. a pharmaceutically-acceptable carrier.

Suitable diagnostic and therapeutic metals include paramagnetic metal ions, gamma-emitting radioisotopes, positron-emitting radioisotopes, and x-ray absorbers.

Suitable paramagnetic metal ions include Gd(III), Dy(III), Fe(III), and Mn(II).

Suitable gamma-emitting radioisotope or positron-emitting radioisotope include $^{62}$Cu, $^{64}$Cu, $^{67}$Cu, $^{67}$Ga, $^{68}$Ga, $^{99m}$Tc, $^{95}$Tc, $^{111}$In, $^{90}$Y, $^{149}$Pr, $^{153}$Sm, $^{159}$Gd, $^{166}$Ho, $^{169}$Yb, $^{177}$Lu, $^{186}$Re, $^{188}$Re, and $^{213}$Bi, preferably, $^{99m}$Tc, $^{111}$In, and $^{213}$Bi.

Suitable x-ray absorbers include Re, Sm, Ho, Lu, Pm, Y, Bi, Pd, Gd, La, Au, Au, Yb, Dy, Cu, Rh, Ag, and Ir.

The conjugates of the invention are formed by contacting, preferably with simple mixing, the desired metal with the desired complex of the invention.

Compositions

The compounds and the conjugates of the invention may be used as a neat composition or as a composition containing at least one pharmaceutically acceptable carrier. Generally, the residue of compound of Formula I or Formula II, or a pharmaceutically acceptable salt thereof, will be present at a level of from about 0.1%, by weight, to about 90% by weight, based on the total weight of the composition, based on the total weight of the composition. Preferably, the residue of compound of Formula I or Formula II or a pharmaceutically acceptable salt thereof will be present at a level of at least about 1%, by weight, based on the total weight of the composition. More preferably, the residue of compound of Formula I or Formula II or a pharmaceutically acceptable salt thereof will be present at a level of at least about 5%, by weight, based on the total weight of the composition. Even more preferably, the residue of compound of Formula I or Formula II or a pharmaceutically acceptable salt thereof will be present at a level of at least about 10%, by weight, based on the total weight of the composition. Yet even more preferably, the residue of compound of Formula I or Formula II or a pharmaceutically acceptable salt thereof, will be present at a level of at least about 25%, by weight, based on the total weight of the composition.

Such compositions are prepared in accordance with acceptable pharmaceutical procedures, such as described in *Remington's Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

In another embodiment, the invention is directed to compositions, comprising:

a. a conjugate, comprising:
   i. at least one targeting moiety selected from the group consisting of peptide, protein, and amine-surface functional dendrimer;
   ii. a residue of a compound of Formula I or Formula II or a pharmaceutically acceptable salt thereof;
      wherein said compound is covalently linked to said targeting moiety; and
   iii. a diagnostic or therapeutic metal; and
b. a pharmaceutically-acceptable carrier.

Pharmaceutically acceptable carriers, adjuvants, and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, TRIS (tris(hydroxymethyl)amino-methane), partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

In some cases, depending on the dose and rate of injection, the binding sites on plasma proteins may become saturated with prodrug and activated agent. This leads to a decreased fraction of protein-bound agent and could compromise its half-life or tolerability as well as the effectiveness of the agent. In these circumstances, it is desirable to inject the prodrug agent in conjunction with a sterile albumin or plasma replacement solution. Alternatively, an apparatus/syringe can be used that contains the contrast agent and mixes it with blood drawn up into the syringe; this is then re-injected into the patient.

The conjugates and pharmaceutical compositions of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term "parenteral" as used herein includes subcutaneous, intravenous, intramuscular, intra-articular, intra-synovial, intrasternal, intrathecal, intrahepatic, intralesional and intracranial injection or infusion techniques.

When administered orally, the pharmaceutical compositions of this invention may be administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, when administered in the form of suppositories for rectal administration, the pharmaceutical compositions of this invention may be prepared by mixing the agent with a suitable non-irritating excipient that is solid at room temperature but liquid at rectal temperature and therefore will melt in the rectum to release the drug. Such materials include cocoa butter, beeswax and polyethylene glycols.

As noted before, the pharmaceutical compositions of this invention may also be administered topically, especially when the target of treatment includes areas or organs readily accessible by topical application, including the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

For administration by nasal aerosol or inhalation, the pharmaceutical compositions of this invention are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

For intravenous and other types of administration, acceptable dose ranges range from about 0.001 to about 1.0 mmol/kg of body weight, with the preferred dose of the active ingredient compound ranging from about 0.001 to about 0.5 mmol/kg of body weight. Even more preferred is from about 0.01 to about 0.1 mmol/kg, and the most preferred dose of the active ingredient compound is from about 0.02 and to about 0.05 mmol/kg.

As the skilled artisan will appreciate, lower or higher doses than those recited above may be required. Specific dosage regimens for any particular patient will depend upon a variety of factors, including the activity of the specific compound employed, the age, body weight, general health status, sex, diet, and time of administration, rate of excretion, drug combination and the judgment of the treating physician.

Kits

In yet other embodiments, the invention is directed to kits for detecting, imaging, monitoring, or treating a disease or condition in a patient comprising:

a. a complex comprising:
   i. at least one targeting moiety selected from the group consisting of peptide, protein, and amine-surface functional dendrimer; and
   ii. a residue of a compound of Formula I or Formula II or a pharmaceutically acceptable salt thereof;
   wherein said compound is covalently linked to said targeting moiety;
b. a therapeutic or diagnostic metal;
c. an optional pharmaceutically-acceptable carrier; and
d. instructions for preparing a composition comprising a therapeutic or diagnostic agent for detecting, imaging, monitoring, or treating a disease or condition in a patient.

The inclusion of one or more optional components in the kit will frequently improve the ease of synthesis of the therapeutic and diagnostic agent by practicing end user, the ease of manufacturing the kit, the shelf-life of the kit, or the stability and shelf-life of the diagnostic metal. The improvement achieved by the inclusion of an optional component in the formulation must be weighed against the added complexity of the kit and added cost to manufacture the kit. One or more vials that contain all or part of the formulation can independently be in the form of a sterile solution or a lyophilized solid.

Buffers useful in the preparation of the therapeutic and diagnostic agents and kits thereof include but are not limited to phosphate, citrate, sulfosalicylate, and acetate. A more complete list can be found in the *United States Pharmacopeia*.

Lyophilization aids useful in the preparation of the therapeutic and diagnostic agents and kits thereof include but are not limited to mannitol, lactose, sorbitol, dextran, Ficoll, and polyvinylpyrrolidine (PVP).

Stabilization aids useful in the preparation of therapeutic and diagnostic agents and kits thereof include but are not limited to ascorbic acid, cysteine, monothioglycerol, sodium bisulfite, sodium metabisulfite, gentisic acid, and inositol.

Solubilization aids useful in the preparation of therapeutic and diagnostic agents and kits thereof include but are not limited to ethanol, glycerin, polyethylene glycol, propylene glycol, polyoxyethylene sorbitan monooleate, sorbitan monoloeate, polysorbates, poly(oxyethylene)-poly(oxypropylene)poly(oxyethylene) block copolymers (Pluronics) and lecithin. Preferred solubilizing aids are polyethylene glycol, and Pluronics copolymers.

Bacteriostats useful in the preparation of therapeutic and diagnostic agents and kits thereof include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or coligand and so forth.

The predetermined amounts of each component in the formulation are determined by a variety of considerations that are in some cases specific for that component and in other cases dependent on the amount of another component or the presence and amount of an optional component. In general, the minimal amount of each component is used that will give the desired effect of the formulation. The desired effect of the formulation is that the practicing end user can synthesize the therapeutic or diagnostic agent and have a high degree of certainty that the therapeutic or diagnostic agent can be injected safely into a patient and will provide a therapeutic effect or diagnostic information about the disease state of that patient.

The kits of the present invention can also contain written instructions for the practicing end user to follow to synthesize the therapeutic or diagnostic agents. These instructions may be affixed to one or more of the vials or to the container in which the vial or vials are packaged for shipping or may be a separate insert, termed the package insert.

X-ray contrast agents and metallopharmaceuticals for magnetic resonance imaging contrast agents are provided to the end user in their final form in a formulation contained typically in one vial, as either a lyophilized solid or an aqueous solution. The end user reconstitutes the lyophilized solid with water or saline and withdraws the patient dose or simply withdraws the dose from the aqueous solution formulation as provided.

Methods of Use

In yet other embodiments, the invention is directed to kits for detecting, imaging, monitoring, or treating a disease or condition in a patient comprising:
a. a conjugate comprising:
  i. at least one targeting moiety selected from the group consisting of peptide, protein, and amine-surface functional dendrimer; and
  ii. a residue of a compound of Formula I or Formula II or a pharmaceutically acceptable salt thereof;
  iii. a diagnostic or therapeutic metal;
    wherein said compound is covalently linked to said targeting moiety;
b. an optional pharmaceutically-acceptable carrier; and
c. instructions for preparing a composition comprising a diagnostic agent for detecting, imaging, monitoring, or treating a disease or condition in a patient.

In other embodiments, the invention is directed to methods of detecting, imaging or monitoring cancer in a patient, comprising the steps of:
a. administering to said patient a conjugate described above; and
b. acquiring an image of a site of concentration of said conjugate in the patient by a diagnostic imaging technique.

Preferable, the diagnostic imaging technique is magnetic resonance imaging, single photon emission imaging, or positron emission tomographic imaging.

In other embodiments, the invention is directed to methods of detecting, imaging or monitoring thrombi in a patient, comprising the steps of:
a. administering to said patient a conjugate described above; and
b. acquiring an image of a site of concentration of said conjugate in the patient by a diagnostic imaging technique.

Preferable, the diagnostic imaging technique is magnetic resonance imaging, single photon emission imaging, or positron emission tomographic imaging.

In yet other embodiments, the invention is directed to methods of treating cancer, comprising the step of:
administering to a patient in need thereof an effective amount of a conjugate described above.

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Preparation of N—[(R)-2-amino-3-(p-nitrophenyl) propyl]trans-(S,S)-cyclohexane-1,2-diamine

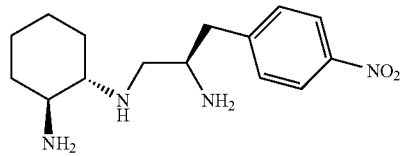

N—[(R)-2-Amino-3-(p-nitrophenyl)propyl]-trans-(S,S)-cyclohexane-1,2-diamine was previously generally prepared in accordance with Wu, C., Kobayashi, H., Sun, B., Yoo, T. M., Paik, C. H., Gansow, O. A., Carrasquillo, J. A., Pastan, I., Brechbiel, M. W.: Stereochemical Influence on the Stability of Radio-Metal Complexes In Vivo. Synthesis and Evaluation of the Four Stereoisomers of 2-(p-nitrobenzyl)-trans-Cy-DTPA. Bioorg. Med. Chem. 1997, 5, 1925-1934. However, the procedure was modified in that the intermediate mono-protected 2,2-diaminocyclohexane was prepared according to a higher yielding route taken from Young. K. Kim, Seok J. Lee and Kyo H. Ahn: New hybrid ligands with a trans-1,2-diaminocyclohexane backbone: competing chelation modes in palladium-catalysed enantioselective allylic alkylation. J. Org. Chem. 2000, 65, 7807-7813.

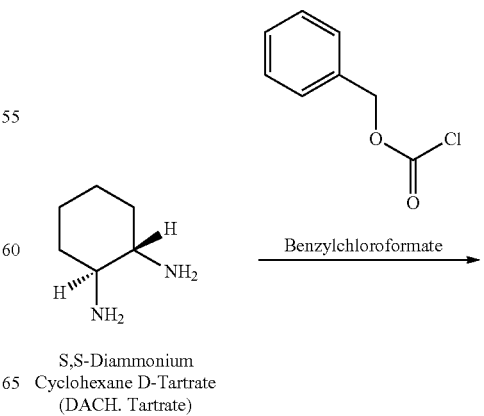

S,S-Diammonium Cyclohexane D-Tartrate (DACH. Tartrate)

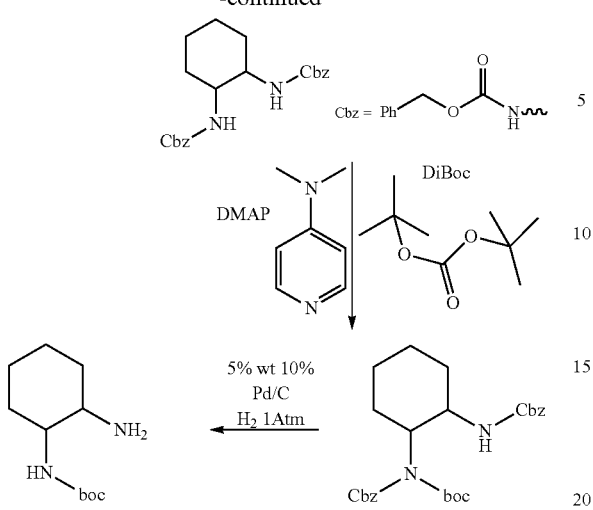

Example 2

Preparation of N—[(R)-2-amino-3-(p-nitrophenyl)propyl]trans-(S,S)-cyclohexane-1,2-diamine-N,N,N',N',N'',N''-pentaethyl-t-butanoate

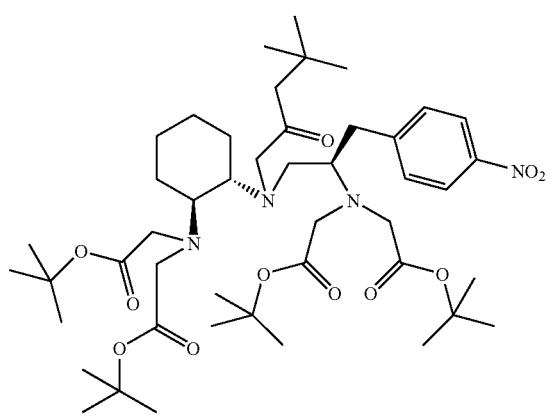 [SMILES: CC(C)(C)CC(=O)CN(C[C@@H](Cc1ccc([N+](=O)[O-])cc1)N(CC(=O)OC(C)(C)C)CC(=O)OC(C)(C)C)[C@H]1CCCC[C@@H]1N(CC(=O)OC(C)(C)C)CC(=O)OC(C)(C)C]

N—[(R)-2-Amino-3-(p-nitrophenyl)propyl]-trans-(S,S)-cyclohexane-1,2-diamine. 3HCl (2 g, 5 mmol) stirred in acetonitrile (50 cm³) with K₂CO₃ (6.21 g, 45 mmol) was treated with t-butylbromoacetate (5.17 cm³, 6.83 g, 35 mmol) and stirred vigorously for 3 days. The solvent was evaporated at reduced pressure, ethylether (100 cm³) added and the mixture filtered. The inorganic salts were washed with additional portions of diethyl ether (3×10 cm³) and the filtrate evaporated at reduced pressure to a viscous orange oil. Purification was achieved on a silica gel column (previously treated with a mixture of water (10%) and ethanol (90%) then rinsed with 100% ethanol followed by ethyl acetate) eluting with 30% ammonia in ethanol:ethyl acetate:hexane 1:1:16 to 1:1:8 gradient.

Example 3

Preparation of N—[(R)-2-Amino-3-(p-aminophenyl)propyl]trans-(S,S)-cyclohexane-1,2-diamine-N,N,N',N',N'',N''-pentaethyl-t-butanoate

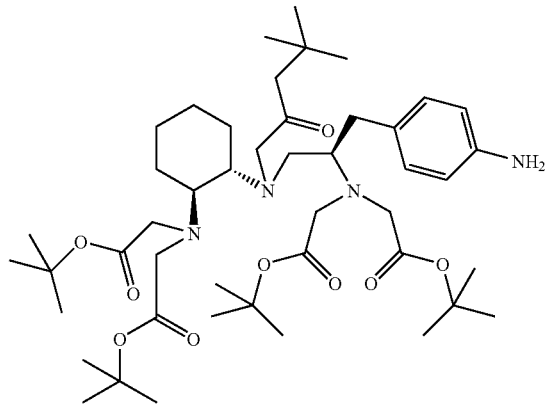 [SMILES: CC(C)(C)CC(=O)CN(C[C@@H](Cc1ccc(N)cc1)N(CC(=O)OC(C)(C)C)CC(=O)OC(C)(C)C)[C@H]1CCCC[C@@H]1N(CC(=O)OC(C)(C)C)CC(=O)OC(C)(C)C]

10% palladium on carbon was placed in an all glass hydrogenation vessel with ethanol (20 cm³) filled with hydrogen. After saturation of the catalyst with hydrogen a solution of N—[(R)-2-Amino-3-(p-nitrophenyl)propyl]-trans-(S,S)-cyclohexane-1,2-diamine-N,N,N',N',N'',N''-pentaethyl-t-butanoate (2.7 g, 3.2 mmol) in ethanol (25 cm³) was injected and pressure maintained at room pressure over 8 hours by periodic refilling of hydrogen. The mixture was left vigorously stirring overnight then filtered through celite, washing with ethanol (5×5 cm³). The filtrate was evaporated at reduced pressure to give a pale yellow oil. The product was purified on neutral alumina eluting with hexane:ethyl acetate:NH₃ in ethanol 18:2:1 yielding a colorless oil after evaporation.

Example 4

Preparation of N—[(R)-2-Amino-3-(p-aminophenyl-N-{5-oxopentanoic acid}propyl]-trans-(S,S)-cyclohexane-1,2-diamine-N,N,N',N',N'',N''-pentaethyl-t-butanoate

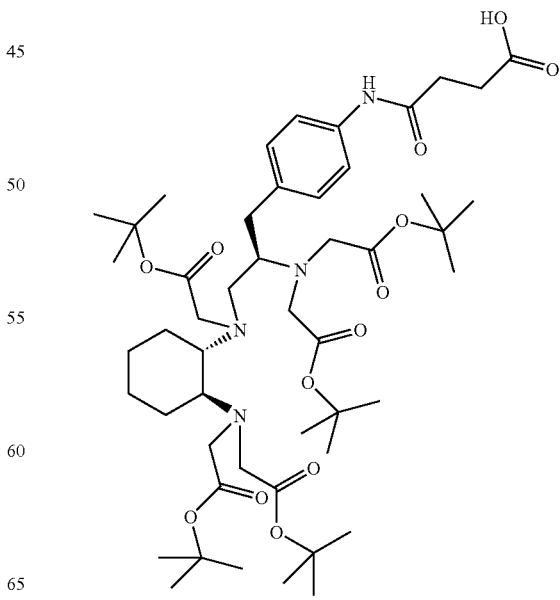

N—[(R)-2-Amino-3-(p-amino phenyl)propyl]-trans-(S,S)-cyclohexane-1,2-diamine-N,N,N',N',N'',N''-pentaethyl-t-butanoate (1.85 g, 2.22 mmol), an excess of glutaric anhydride (0.507 g, 4.45 mmol) were mixed in benzene (30 cm³) with stirring overnight. A further portion of benzene was added (30 cm³) and was washed with 0.1M Na₂HPO₃ (1×30 cm³) followed by washing with 0.1M NaH₂PO₃. The organic fraction was dried over Na₂SO₄, filtered then evaporated at reduced pressure to yield a pale brown oil. The product was further purified by chromatography on a silica gel column (previously treated with a mixture of water (10%) and ethanol (90%) then rinsed with 100% ethanol followed by ethyl acetate) eluting with ethanol:hexane 1:5 to 1:1 gradient, yielding after evaporation at reduced pressure a glassy, colorless solid.

Example 5

Preparation of N—[(R)-2-Amino-3-(p-5-[(2,5-dioxopyrrolidin-1-yl)oxy]-5-oxo-N-phenylpentanamide)propyl]-trans-(S,S)-cyclohexane-1,2-diamine-N,N,N',N'',N''-penta-t-butylacetate Compound of Formula I

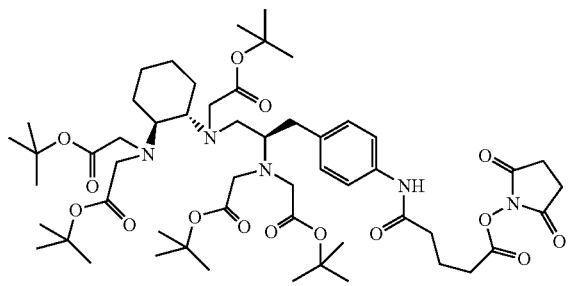 [SMILES: CC(C)(C)OC(=O)CN(CC(=O)OC(C)(C)C)[C@H](Cc1ccc(NC(=O)CCCC(=O)ON2C(=O)CCC2=O)cc1)CN(CC(=O)OC(C)(C)C)[C@H]1CCCC[C@@H]1N(CC(=O)OC(C)(C)C)CC(=O)OC(C)(C)C]

1-[3-(dimethylamino)propyl]-3-ethylcarbodiimide hydrochloride (0.286 g, 1.5 mmol), N-hydroxy succinimide (0.151 g, 1.3 mmol) and N—[(R)-2-Amino-3-(p-aminophenyl-N-{5-oxopentanoic acid})propyl]-trans-(S,S)-cyclohexane-1,2-diamine-N,N,N',N'',N''-penta-t-butylacetate (1.13 g, 1.2 mmol) were stirred in a mixture of ethyl acetate (30 cm³) and DMF (10 cm³) overnight. The reaction mixture was then diluted with ethyl acetate (30 cm³) and cooled in an ice bath. The cooled mixture was washed with 5% w/v aqueous NaHCO₃ solution (2×20 cm³) ice cold and then with ice cold water (2×20 cm³). The organic fraction was dried over Na₂SO₄, filtered and evaporated at reduced pressure to yield a glassy pale yellow solid. No further purification was performed on this compound.

Example 6

Preparation of Compound of Formula II

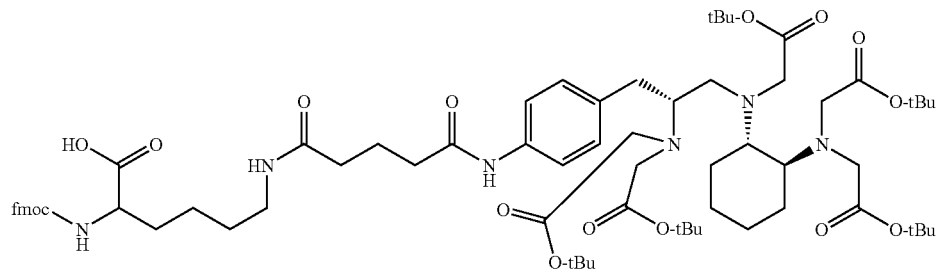

A suspension of an α-Fmoc-lysine (0.024 g) in dimethyl formamide (1 cm³) was treated with the compound of Formula I from Example 5 over a period of 30 minutes the solution cleared. The mixture was stirred overnight then ethyl acetate (20 cm³) added and the mixture washed with 0.1 M NaH₂PO₃ (4×10 cm³).

Example 7

Complex Formation

The compound of Formula I was tested as a bioconjugation reagent with a sample of octatreotide. A mass spectrum of the complex formed indicated successful labeling of the unprotected amine terminus to form the complex of the compound of Formula I and octatreotide. NMR spectra of the unlabeled and labeled complex also confirmed complex formation.

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:
1. A complex, comprising:
 (a) at least one targeting moiety selected from the group consisting of peptide, protein, and an amine-surface functional dendrimer which is covalently bonded to

(b) a compound of formula I or II

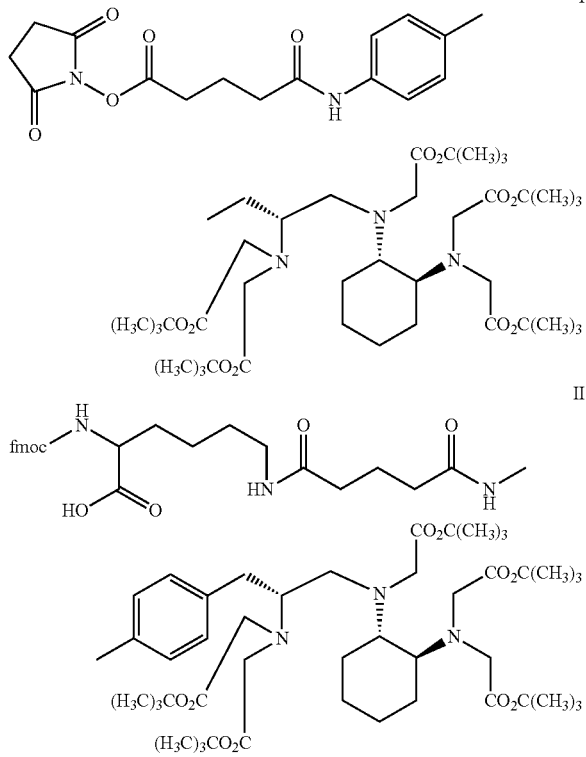

or a pharmaceutically acceptable salt thereof;
wherein fmoc is 9-fluorenylmethoxycarbonyl.

2. A complex according to claim 1,
wherein said targeting moiety is PAMAM dendrimer, octatreotide, bombesin, or α-melanocyte stimulating hormone.

3. A complex according to claim 1,
wherein said compound is linked to said targeting moiety via a terminal amino group on said targeting moiety.

4. A complex according to claim 3,
wherein said compound is linked to said targeting moiety via an N-terminus, a lysine residue, or amine.

5. A complex according to claim 1,
wherein said compound is a compound of Formula I or a pharmaceutically acceptable salt thereof.

6. A complex according to claim 1,
wherein said compound is a compound of Formula II or a pharmaceutically acceptable salt thereof.

7. A conjugate, comprising:
(a) a complex according to claim 1; and
(b) a diagnostic or therapeutic metal.

8. A conjugate according to claim 7,
wherein said diagnostic or therapeutic metal is selected from the group consisting of a paramagnetic metal ion, a gamma-emitting radioisotope, a positron-emitting radioisotope, and an x-ray absorber.

9. A conjugate according to claim 8,
wherein said paramagnetic metal ion is selected from the group consisting of: Gd(III), Dy(III), Fe(III), and Mn(II).

10. A conjugate according to claim 8,
wherein said diagnostic or therapeutic metal is a gamma-emitting radioisotope or positron-emitting radioisotope selected from the group consisting of: $^{62}$Cu, $^{64}$Cu, $^{67}$Cu, $^{67}$Ga, $^{68}$Ga, $^{99m}$Tc, $^{95}$Tc, $^{111}$In, $^{90}$Y, $^{149}$Pr, $^{153}$Sm, $^{159}$Gd, $^{166}$Ho, $^{169}$Yb, $^{177}$Lu, $^{186}$Re, $^{188}$Re, and $^{213}$Bi.

11. A conjugate according to claim 10,
wherein said diagnostic or therapeutic metal is $^{99m}$Tc.

12. A conjugate according to claim 10,
wherein said diagnostic or therapeutic metal is $^{111}$In.

13. A conjugate according to claim 10,
wherein said diagnostic or therapeutic metal is $^{213}$Bi.

14. A conjugate according to claim 8,
wherein said x-ray absorber is a metal selected from the group consisting of: Re, Sm, Ho, Lu, Pm, Y, Bi, Pd, Gd, La, Au, Au, Yb, Dy, Cu, Rh, Ag, and Ir.

15. A composition, comprising:
(a) a complex according to claim 1; and
(b) a pharmaceutically-acceptable carrier.

16. A composition, comprising:
(a) a complex according to claim 1; and
(b) a pharmaceutically-acceptable carrier.

17. A composition, comprising:
(a) a conjugate according to claim 7 or a pharmaceutically acceptable salt thereof; and
(b) a pharmaceutically-acceptable carrier.

18. A kit comprising:
(a) a complex according to claim 1;
(b) a therapeutic or diagnostic metal;
(c) an optional pharmaceutically-acceptable carrier; and
(d) instructions for preparing a composition comprising a therapeutic or diagnostic agent.

19. A kit comprising:
(a) a conjugate according to claim 7 or a pharmaceutically acceptable salt thereof;
(b) an optional pharmaceutically-acceptable carrier; and
(c) instructions for preparing a composition comprising a therapeutic or diagnostic agent.

20. A method of detecting, imaging, or monitoring cancer in a patient, comprising the steps of:
(a) administering to said patient a conjugate according to claim 8 or a pharmaceutically acceptable salt thereof; and
(b) acquiring an image of a site of concentration of said conjugate in the patient by a diagnostic imaging technique wherein said diagnostic imaging technique is magnetic resonance imaging, single photoemission imaging, or positron emission tomographic imaging.

21. A method of detecting, imaging or monitoring thrombi in a patient, comprising the steps of:
(a) administering to said patient a conjugate according to claim 7 or a pharmaceutically acceptable salt thereof; and
(b) acquiring an image of a site of concentration of said conjugate in the patient by a diagnostic imaging technique.

22. A method according to claim 21,
wherein said diagnostic imaging technique is magnetic resonance imaging, single photon emission imaging, or positron emission tomographic imaging.

23. A method of treating cancer, comprising the step of:
administering to a patient in need thereof an effective amount of a conjugate according to claim 7 or a pharmaceutically acceptable salt thereof.

24. A method of treating thrombosis, comprising the step of:
administering to a patient in need thereof an effective amount of a conjugate according to claim 7 or a pharmaceutically acceptable salt thereof.

* * * * *